(12) United States Patent
Sternby

(10) Patent No.: US 7,435,235 B2
(45) Date of Patent: Oct. 14, 2008

(54) BLOOD TREATMENT EQUIPMENT, METHOD, AND SOFTWARE PROGRAM FOR CONTROLLING INFUSION IN BLOOD TREATMENT EQUIPMENT

(75) Inventor: Jan Peter Sternby, Lund (SE)

(73) Assignee: Gambro Lundia AB (SE)

( * ) Notice: Subject to any disclaimer, the term of this patent is extended or adjusted under 35 U.S.C. 154(b) by 344 days.

(21) Appl. No.: 11/121,940

(22) Filed: May 5, 2005

(65) Prior Publication Data
US 2005/0251086 A1 Nov. 10, 2005

Related U.S. Application Data

(60) Provisional application No. 60/521,508, filed on May 7, 2004.

(51) Int. Cl.
*A61M 37/00* (2006.01)
*C02F 1/44* (2006.01)
*C02F 1/00* (2006.01)
*A61M 1/00* (2006.01)

(52) U.S. Cl. ............... 604/6.09; 604/4.01; 604/5.01; 604/5.04; 210/645; 210/646; 210/739; 210/746; 422/44

(58) Field of Classification Search ............ 604/4.01, 604/5.01, 5.04, 6.09, 6.11; 210/645, 646, 210/600, 633, 739, 944, 746, 203, 416.1, 210/433.1, 500.21; 422/44; 600/322; 436/178
See application file for complete search history.

(56) References Cited

U.S. PATENT DOCUMENTS 5,507,723 A 4/1996 Keshaviah
5,567,320 A 10/1996 Goux et al.

(Continued)

FOREIGN PATENT DOCUMENTS

EP 0 547 025 A1 6/1993

(Continued)

OTHER PUBLICATIONS

David et al., "Pre-Postdilution Haemofiltration", Nephrol Dial Transplant, vol. 4, pp. 37-40, (1989).

(Continued)

*Primary Examiner*—Leslie R Deak
(74) *Attorney, Agent, or Firm*—Finnegan, Henderson, Farabow, Garrett & Dunner L.L.P.

(57) ABSTRACT

A method and blood treatment equipment for controlling infusion are described. The equipment comprising: an extracorporeal blood circuit, a pre-infusion line connected to the blood circuit upstream a blood treatment unit, a post-infusion line connected to the blood circuit downstream the blood treatment unit, a waste line connected to an outlet of the treatment unit. A sensor operates on the waste line for sensing at least one fluid parameter and is connected to a control unit which commands a fluid flow through said pre-infusion line and through said post-infusion line. The control unit also determines from values of said fluid parameter at least a corresponding value of an efficiency parameter relating to blood depuration efficiency of the blood treatment unit, and controls the flow rate of at least one of the fluid flows through said infusion lines as a function of the value of the efficiency parameter. A software program for execution by the control unit is also claimed.

57 Claims, 2 Drawing Sheets

U.S. PATENT DOCUMENTS

| | | | |
|---|---|---|---|
| 5,744,031 A * | 4/1998 | Bene | 210/321.71 |
| 6,187,207 B1 * | 2/2001 | Brauer | 210/739 |
| 6,635,026 B1 | 10/2003 | Béné | |
| 6,814,864 B1 | 11/2004 | Favre et al. | |
| 6,824,524 B1 | 11/2004 | Favre | |

FOREIGN PATENT DOCUMENTS

| | | |
|---|---|---|
| EP | 0 658 352 A1 | 6/1995 |
| EP | 0 711 182 B1 | 5/1996 |
| EP | 0 920 877 A1 | 6/1999 |
| EP | 1097724 | 5/2001 |
| EP | 1 108 438 A1 | 6/2001 |
| EP | 1175917 | 1/2002 |
| EP | 1175917 A1 | 1/2002 |
| WO | WO 98/55166 * | 12/1998 |
| WO | WO 00/51664 | 9/2000 |
| WO | WO 01/08723 A1 | 2/2001 |
| WO | WO 01/32238 A2 | 5/2001 |

OTHER PUBLICATIONS

International Search Report for International Application No. PCT/IB2005/001007.

* cited by examiner

BLOOD TREATMENT EQUIPMENT, METHOD, AND SOFTWARE PROGRAM FOR CONTROLLING INFUSION IN BLOOD TREATMENT EQUIPMENT

CROSS REFERENCE TO RELATED APPLICATION

This claims the right to priority based on Provisional Patent Application No. 60/521,508, filed on May 7, 2004, and entitled "Blood Treatment Equipment, Method and Software Program for Controlling Infusion in Blood Treatment Equipment," the entire content of which is incorporated herein by reference.

DESCRIPTION OF THE INVENTION

1. Field of the Invention

The present invention relates to blood treatment equipment, method and software program for controlling infusion in blood treatment equipment. The present invention finds application in equipment for treating blood wherein a pre and a post infusion line are provided, respectively upstream and downstream of a blood treatment unit. While the invention is particularly suitable in blood treatments such as hemofiltration or hemodiafiltration, it is not excluded application of the invention in any extracorporeal blood treatment wherein blood is treated in a treating unit and wherein infusion of a substitution fluid is provided for.

2. Prior Art

As it is known in the art patients suffering from kidney failure or renal insufficiency, or patient suffering of particular pathologies should be submitted to specific treatments, mainly addressed to clear their body from undesired substances and excess of fluid.

More in detail, it is known to treat blood in an extracorporeal circuit in order to carry out ultrafiltration, hemodialysis, hemofiltration, hemodiafiltration, plasmapheresis, blood component separation, blood oxygenation, etc. Normally, blood is removed from a blood vessel, sent into a withdrawal line of an extracorporeal circuit, passed through a blood-treating unit and returned to another or to the same blood vessel.

In particular referring to the field of renal insufficiency treatment, therapies such as hemofiltration and hemodiafiltration have found more and more consent and actual application on patients, due to their ability of joining clearance of both small and big particles, as well as efficient fluid removal. In hemofiltration mode, blood circulates in one chamber of a treatment unit (the hemofilter) formed by two chambers divided by a semi-permeable membrane; a relevant volume of water (higher than in case of pure ultrafiltration) is removed from blood by creating a pressure difference between the first and the second chamber of the hemofilter. An infusion line entering into the blood circuit partially replaces the removed plasmatic water. In this case, blood purification is achieved by convective transfer of molecules. The molecules are removed from the blood by the water migrating in to the second chamber of the. hemofilter.

In case of hemodiafiltration, a dialysis fluid is also sent into the second chamber of the hemofilter, thereby combining the convective purification with the diffusive purification of a dialysis treatment.

Recently, referring to hemofiltration or hemodiafiltretion treatments, it has been found that a combination of two infusions, one carried out upstream of the treatment unit and one downstream of the treatment unit allows achievement of the highest clearance for a given quantity of overall infusion fluid.

In other words, a user or a physician can prescribe a total infusion flow rate and then split the flow into a pre-infusion and a post-infusion portion in order to achieve high clearance of solutes from the patient's blood.

It is also known in the art, from EP1175917, to combine pre and post infusion in hemofiltration treatments with a control system that can modify repartition of flow in the pre and post infusion lines as a function of a patient's hematocrit or treatment unit trans membrane pressure (TMP). This system, however, is designed to keep a patient's TMP or hematocrit levels below undue thresholds during treatment.

Finally, EP0711182 shows a blood treatment system provided with means for measuring the actual metabolite concentration in the waste line out of the treatment unit to determine metabolite clearance. A control unit receives the detected metabolite concentration and operates on blood flow rate or on dialysate flow rate with the aim to increase metabolite clearance as much as possible.

SUMMARY OF THE INVENTION

While the prior art provided solutions having the provision for a pre and a post infusion line, the prior art solutions either had no control of the pre and post infusion flows as a function of other parameters, or had pre or post flow rates in the infusion lines controlled according to pre-fixed set values, or had pre and post infusion lines flow rates controlled in order to avoid passing threshold values of certain specific parameters (hematocrit or trans membrane pressure).

On the other hand, it is an object of the present invention to provide for a method, and for an equipment, which during treatment allow to combine and modify pre and/or post-infusion flows in order to improve solute clearance.

Moreover it is a further object of the invention providing a technical solution, which can be implemented with no burden employing conventional sensors and controls present in blood treatment machines.

Furthermore it is an object of the invention to offer a system not inherently limited by a pre-fixed total amount of infusion fluid.

The above and other objects are reached by a blood treatment equipment, by a method, by a software program for controlling infusion in blood treatment equipment as disclosed in one or more of the appended claims.

In the following sections, preferred embodiments of the invention will be described with reference to the accompanying drawings.

DESCRIPTION OF PREFERRED EMBODIMENTS

Figure 1:
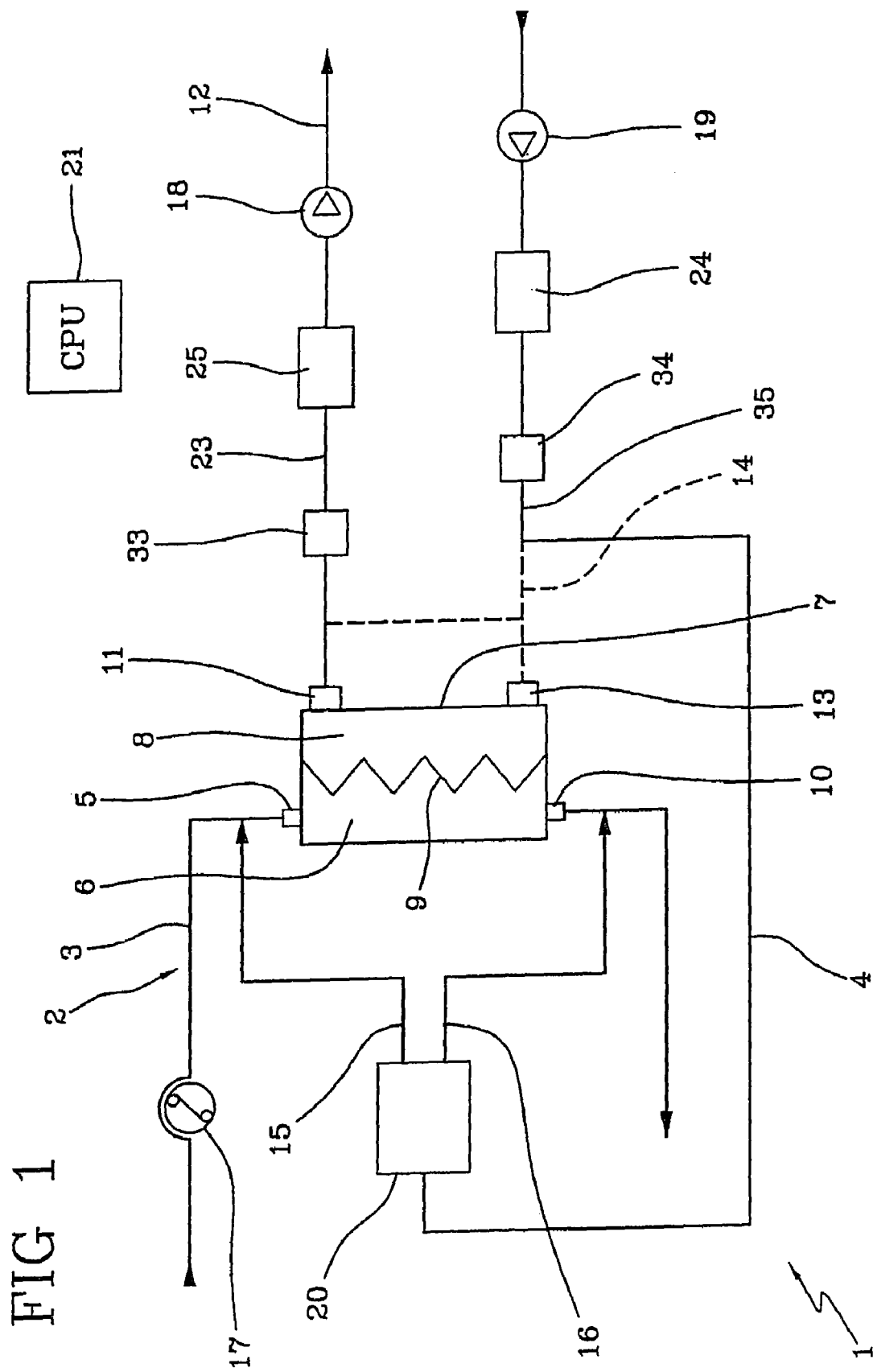
FIG. 1 is a schematic view of blood treatment equipment according to an embodiment of the invention.

With reference to the enclosed drawings a blood treatment equipment has been identified with reference numeral 1.

The equipment 1 comprises an extracorporeal blood circuit 2 to be connected in use to the cardiovascular system of a patient to be treated (not shown in the drawings). In practice, the patient can be connected to the extracorporeal circuit via one or two needles, a catheter, a cannula, an implanted artificial access device or other equivalent access means, which allows withdrawal and return of blood from and to the patient. The extracorporeal circuit of the embodiment shown in the appended drawings presents an arterial line 3, for withdrawing blood to be treated from the patient and a venous line 4 for returning treated blood into the patient. A downstream end of the arterial line is connected to the inlet 5 of a first chamber 6 of a treatment unit 7 also comprising a second chamber 8 separated by the first chamber 6 by means of a semipermeable membrane 9. An outlet 10 of the first chamber 6 of said treatment unit 7 is also connected to an upstream end of the venous line. The second chamber 8 of the treatment unit presents an outlet 11, which is connected to a waste line 12. In case the equipment is intended to run a hemodiafiltration treatment the second chamber also presents an inlet 13 for receiving a fresh dialysis liquid line 14.

The equipment 1 also presents a pre-infusion line 15 connected to the blood circuit upstream the blood treatment unit, and a post-infusion line 16 connected to the blood circuit downstream the blood treatment unit 7. In the blood treatment field the pre-infusion and post-infusion lines are also referred to as pre-dilution and post-dilution lines respectively.

Embodiment of FIG. 1

In the embodiment shown in FIG. 1 the various fluids are in use circulated through the respective lines by the following devices: a blood pump 17 operating on the extracorporeal blood circuit, a waste pump 18 operating on the waste line, a fresh liquid pump 19 (in this embodiment the liquid is prepared online, though it is clear for those skilled in the art that infusion or dialysis liquid can come from respective containers of pre-prepared liquid) sending liquid both to the dialysis line 14 (if present and used) and to the two infusion lines 15 and 16; notice that in the embodiment shown a three ports distribution device 20 is present which is designed to receive the infusion liquid at the inlet and split it into respective quantities sent to the pre-infusion outlet port and to the post-infusion outlet port according to the instructions received by the control unit 21, which also controls pumps 17, 18 and 19. Device 20 can be for instance a three way proportional valve. Alternatively it can be a simple junction dividing a common tubing in the two infusion lines with occlusion elements (rollers or pinch elements) acting on respective portions of the two infusion lines, or using a tubing dividing into two lines the device 20 can be defined by two different pumps, either one for the total flow and one in one of the two lines 15 and 16, or one in each of the two lines 15 and 16. Refering to the circuit of FIG. 1 when adapted for on-line pre/post HF or HDF, the working equipment 1 can be the following. Blood is pumped at a flow rate Of $Q_b$ into the blood treatment unit or dialyzer 7, and then continues out of the dialyzer, now with a flow rate of $Q_b$−WL, where WL is the weight loss rate. The venous pressure $P_v$ is measured at the outlet by a sensor 22. The dialysis fluid is pumped at flow rate $Q_d$ by pump 19 into the dialyzer. Part of the flow, $Q_{inf}$ is diverted before the dialyzer to be used as substitution fluid, and the rest passes the dialyzer and is pumped out by pump 18. The dialysate pressure $P_d$ is measured at the dialyzer outlet by sensor 23. The diverted substitution fluid goes to the distribution device 20. The substitution fluid is divided by device 20 into one part $Q_i$ for predilution and one part $Q_o$ for postdilution. In case of a machine having on line fluid preparation as the one of FIG. 1, the total ultrafiltration across the dialyzer membrane is controlled by the pump 18 in one of two ways. In volume mode the difference between the flows measured by the flow meters 24 and 25 (note that as possible alternatives to two separate flowmeters a differential flow meter device could be used or balance chamber systems could be adopted, without departing from the sprit of the invention) is used to control the pump so that this difference agrees with the desired weight loss rate WL. In TMP mode the pump 18 instead controls the TMP ($P_v$−$P_d$) to the desired set point. This will create a certain total ultrafiltration (UF) across the dialyzer membrane. The measured flow difference between 24 and 25 is now instead kept at the desired WL by controlling $Q_{inf}$ with the substitution fluid pump. In both cases the patient weight loss is secured by having UF=$Q_{inf}$+WL.

Going in further detail and assuming to adopt the equipment of FIG. 1 for. HF treatment in TMP mode, then the set point for TMP is decided by the user, and is maintained by controlling the fluid outflow pump 18. The venous blood pressure and the fluid pressure after the treatment unit 7 are measured, their difference is the measured TMP, which by a control unit 21 is compared to the TMP set point. The immediate and accumulated difference is used to control the speed of the pump 18 so that TMP is kept at the set point.

The TMP across the treatment unit membrane will determine UF, the amount of fluid that is ultrafiltered from the blood side to the dialysate side. This function will also depend on the chosen membrane (area and permeability) and the properties of the blood entering the dialyzer. The more diluted the blood is, the more ultrafiltration will result at a given TMP.

The maximum filtration that is possible to get in a treatment will be limited by 3 factors: the blood flow rate, the UF capacity of the filter and the available amount of substitution fluid. In postdilution mode it is almost always the blood flow rate that is limiting. When UF is about ¼ to ⅓ of the blood flow rate, the blood becomes so thick and hard to pump that no further UF is possible. In normal postdilution HF and HDF treatments both the capacity of the filter and the available substitution fluid usually exceed this value. In predilution mode the situation is different. Due to the dilution the blood becomes thinner and much easier to filtrate. It is therefore possible to achieve much higher UF rates, and the more filtration we have, the more diluted becomes the blood entering the dialyzer. The limit is then either the water permeability of the filter, or, if this is high, the available amount of substitution fluid.

In postdilution HF clearance equals the UF rate. In predilution HF the dialyzer clearance still equals the UF rate, but since the incoming blood is diluted by the substitution fluid, the "system" clearance, i.e. the clearance of undiluted blood, will be reduced by the dilution factor. This means that postdilution makes more efficient use of the substitution fluid, but on the other hand it is possible to achieve a much higher total UF rate in predilution mode. For a maximum clearance it may therefore in some cases be advantageous not to maximize the postdilution part.

If the available substitution fluid rate is not higher than what can be ultrafiltered in postdilution mode, then it is best to give everything in postdilution. But if a decrease in the postdilution substitution makes possible a sufficiently large increase in the predilution substitution, then this could increase the efficiency of the blood treatment unit, for instance expressed by the filter clearance.

Clearance K (defined here as blood water clearance) can be calculated from the blood flow rate (blood water flow rate) $Q_B$, the predilution flow rate $Q_i$, the postdilution flow rate $Q_o$ and the weight loss rate WL as:

$$K = \frac{Q_B}{Q_B + Q_i}(Q_i + Q_o + WL) \quad (1)$$

We can then rearrange this formula to see how much $Q_i$ has to increase for K to stay unchanged when $Q_o$ decreases:

$$Q_i = \frac{Q_B(K - Q_o - WL)}{Q_B - K} = \frac{Q_B(K - WL)}{Q_B - K} - \frac{Q_B}{Q_B - K}Q_o$$

For unchanged $Q_B$, K and WL we see that $$\Delta Q_i = -\frac{Q_B}{Q_B - K}\Delta Q_o$$

Starting with pure postdilution, clearance (UF) is often about ⅓ of the blood water flow. In such a case the predilution infusion has to increase by 50% more than the decrease in postilution infusion to keep clearance unchanged, i.e. there has to be an extra 50% increase in the total ultrafiltration. This is not unreasonable. As predilution infusion increases, clearance will increase, and the demand for increases in the predilution infusion with decreasing postdilution will be even higher, and there will obviously be a limit at some point.

Normally the UF rate will increase with increasing TMP, even though it may sometimes happen at very low blood flow rates that UF starts to decrease again at high TMPs. In any case, in TMP mode, with a constant TMP, the achieved UF rate for a certain treatment unit will depend on the blood flow rate and the blood properties, here represented by the hematocrit Hct. In reality the protein content and other factors also influence the UF rate, but they will all act similarly to Hct in allowing an increased UF rate as the blood is diluted. The achieved UF rate will also increase if the blood flow rate increases, since the increased flow will decrease the thickness of secondary membranes formed at the membrane surface by protein and cells due to the ultrafiltration. We can therefore for the given dialyzer and TMP set point say that $$UF = f(Q_B + Q_i, Hct)$$

When predilution is increased, the flow rate on the blood side, $Q_B + Q_i$ will increase, and Hct will decrease. Both of these factors will tend to increase UF. Whether this increase is sufficient to increase the clearance or other parameter expression of the treatment unit efficiency can be measured. If clearance is the parameter selected as expression of blood treatment unit efficiency, then a complete in-vivo clearance measurement can be carried out. Alternatively, as efficiency parameter, the change in the conductivity in the waste line can be used (which requires that there is a difference between the inlet dialysate and the blood).

In-vivo clearance (or dialysance if the substance is present not only in blood but also in the treatment fluid) determination can be done according to one of several possible alternatives. All these methods start from determination of the conductivity of the treatment fluid (or alternatively the concentration of at least one specific substance) downstream the treatment unit for then calculating the clearance. By way of non-limiting example, refer to EP1108438, EP0920877, EP0658352, and EP0547025, the specifications of which are herein incorporated by reference. In particular the method of EP0547025 can be adopted wherein a perturbation in the conductivity (or concentration of at least a substance) of a liquid entering the treatment unit (for instance a conductivity perturbation in the form of a long or short step-pulse) and a corresponding perturbation in the effluent waste line is measured. The concentration or conductivity perturbations can be obtained in a machine with on-line preparation by properly controlling at least a concentrate feed system (not shown) which doses the amount of concentrate (typically a mixture of salts) to be added to the liquid in preparation. The concentrate can be in liquid or powder form. From the comparison of the perturbation upstream and downstream the treatment unit, in-vivo clearance or dialysance can be determined.

Notice that if a complete clearance measurement is used with predilution HF or HDF adopting the circuit of FIG. 1, it is necessary that the measurement technique is adapted for use with predilution, since a change in the inlet conductivity will produce two changes in the outlet conductivity, one from the change in the dialysis fluid and one from the change in the substitution fluid.

If alternatively to the complete in-vivo clearance measurement, a measurement of the outlet conductivity alone is adopted, we have the relation derived from equating removal from the blood to increase in the dialysate $$K(C_b - C_i) = (Q_d + UF) \cdot (C_o - C_i) \quad (2)$$

If we want to detect changes in K by measuring $C_o$ we see that $C_i$ must be kept different from $C_b$, otherwise all the conductivities will be equal regardless of the value of K. If $C_b$ and $C_i$ are different, $C_o$ will be somewhere in between since K is smaller than the dialysate flow. A higher clearance will make $C_o$ differ more from $C_i$, and we can thus use the difference as a measure of clearance. It is only necessary to know if the changes made increase or decrease clearance.

Depending upon the method used for detecting the efficiency parameter, for instance clearance, different sensors may be adopted. In FIG. 1, a sensor 33 operates on the waste line for sensing a fluid parameter. The sensed parameter is either conductivity of the fluid passing through the waste line, or concentration of at least one substance contained in the fluid passing through the waste line.

In practice, for achieving conductivity measurements, temperature compensated conductivity cells can be used or substance selective concentration sensors (the detected substances could be electrolytes, metabolites, etcetera).

In the embodiment shown relating to a hemodiafiltration configuration, a further sensor 34 of the same type is also operating upstream the treatment unit on the common portion 35 of the fluid preparation line to detect the same fluid parameter. According to this configuration the two sensors 33 and 34 allow to capture upstream and downstream values for the same parameter. Use of two sensors can be useful if a complete clearance computation is to be done.

A control unit is connected to the sensor or to the sensors 33, 34 for receiving signals relating to values of said fluid parameter. From the values of the fluid parameter the control unit is programmed to perform in-vivo calculation of at least a corresponding value of an efficiency parameter relating to the blood depuration efficiency of the blood treatment unit.

The control unit is also connected to the means for creating a flow rate through the infusion lines for activating said means in order to cause a flow rate through each respective infusion line. The control unit is also programmed to control the flow rate of at least one or both of the fluid flows through said infusion lines as a function of said value of the efficiency parameter.

More in detail, a procedure for optimizing the distribution between predilution and postdilution could then be as follows when using the embodiment of FIG. 1, which is provided with the distribution device 20.

Again assuming the equipment is set for TMP control of the substitution fluid we could start with all the fluid being used in postdilution mode. Either the clearance or the outlet conductivity is measured in this state. A change of known size is then made in the flow distribution (towards predilution: basically predilution flow rate is increased and post-dilution flow rate decreased) and the clearance or outlet conductivity is measured again. If the measurement indicates an increased clearance another change is taken in the same direction and a new measurement is performed. This is continued until no further improvement is gained. In some cases it may happen that no improvement can be gained. If so, this means that it is optimal to use all the fluid for postdilution.

It is possible to improve-this strategy and speed up its convergence by letting the size of the changes in the flow distribution depend on the achieved improvements of the clearance. In the literature there are numerous methods available for the efficient numerical optimization of functions which can be employed for this purpose.

This optimization can be performed either continuously, or intermittently a number of times during the treatment with a constant distribution of the substitution fluid in between the optimizations.

Notice that in case the distribution device 20 utilizes two pumps, or if the distribution of the substitution flow is known by some other method, there is a possibility to do the optimization of pre/post HF without any further measurements, since the clearance can then be calculated on-line using the formula (1) above. It is then not necessary to measure clearance separately. Theoretically this could be done also in HDF: more in detail in case of small $Q_D$ clearance we can calculate clearance even in HDF using equation 1 if we add $Q_D$ inside the parenthesis, while if $Q_D$ is relatively big the clearance formula is then much more complicated and contains a parameter (koA for the treatment unit) that is not known a priori.

Figure 2:
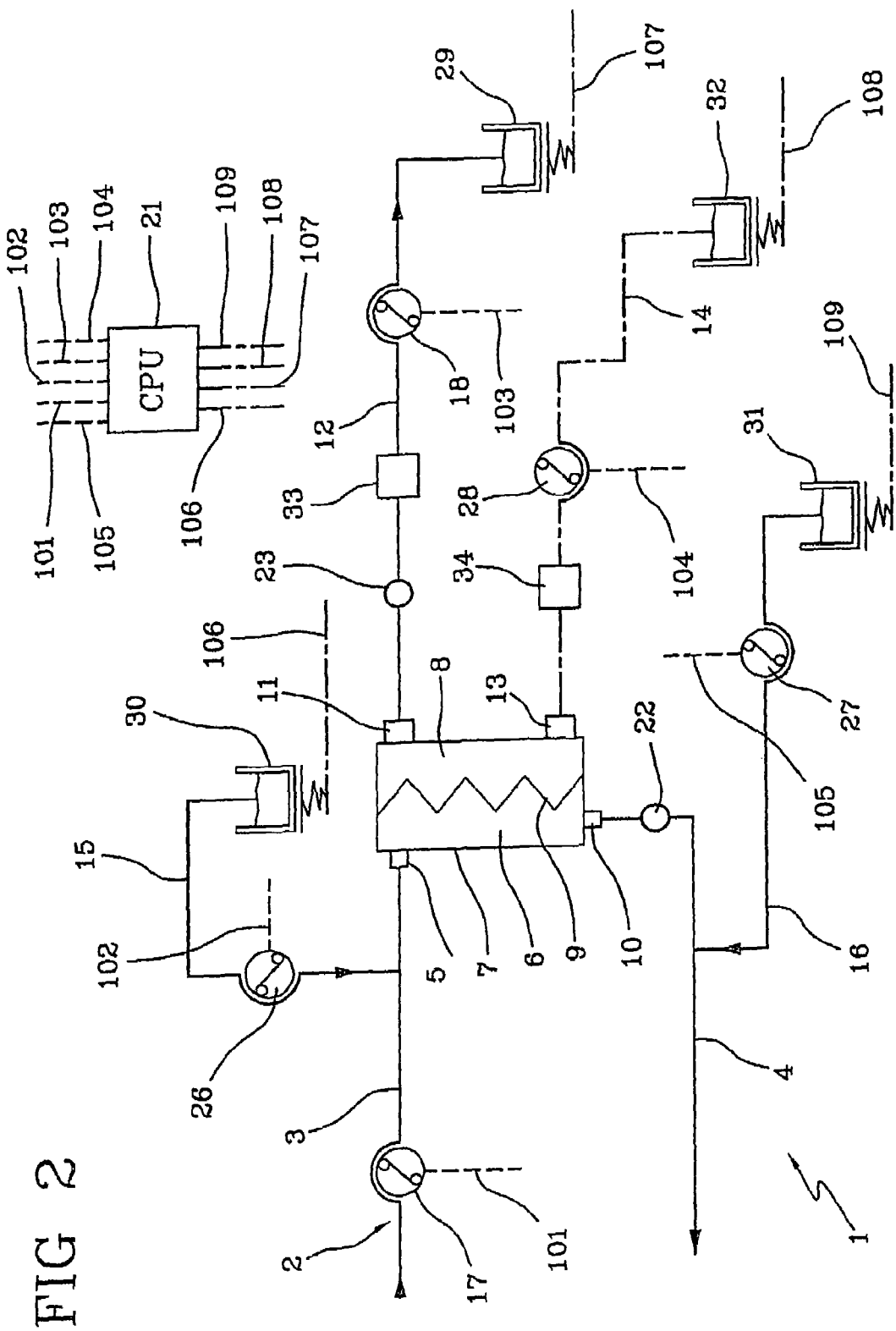
FIG. 2 is a schematic view of blood treatment equipment according to an alternative embodiment of the invention.

Embodiment of FIG. 2

In this embodiment we have that the two infusion lines 15, 16 are separate and that flow within said respective lines is regulated by a corresponding pump 26, 27. A dialysis liquid pump 28 is operating on the dialysis liquid line 14 (in case this line, which is dashed in the attached figures, is actually present and used). As for the previous embodiment a blood pump 17 operates on the extracorporeal blood circuit and a waste pump 18 is active on waste line 12. According to this embodiment fluids are collect in and delivered from respective container: a waste 29 container receives the end of waste line 12, a first infusion container 30 feeds fluid to the pre-infusion line, a second infusion container 31 feeds fluid to the post infusion line 16, a dialysis fluid container 32 feeds the dialysis line 14. Control unit 21 controls all above pumps via control lines 101, 102, 102, 103, 104 and 105.

In terms of fluid balance control and possibility of running a TMP based control, the equipment of FIG. 2 could work according to a procedure similar to the one of FIG. 1 (but for the presence of separate lines/separate pumps for each respective fluid: waste fluid, pre-infusion fluid, post-infusion fluid, dialysis fluid), which will not be hereinafter repeated.

As described for the example of FIG. 1, the equipment of FIG. 2 could also comprise a sensor 33 for sensing a fluid parameter: i.e. either conductivity of the fluid passing through the waste line, or concentration of at least one substance contained in the fluid passing through the waste line.

In practice, temperature compensated conductivity cells or substance selective concentration sensors can be used (the detected substances could be electrolytes, metabolites, etcetera).

In the embodiment shown relating to a hemodiafiltration configuration, the further sensor 34 of the same type is also operating upstream the treatment unit on the dialysis liquid line to detect the same fluid parameter. According to this configuration the two sensors allow to capture upstream and downstream values for the same parameter.

Control unit 21 is also connected to the sensor or to the sensors for receiving signals relating to values of said fluid parameter. From the values of the fluid parameter the control unit is programmed to perform in-vivo calculation of at least a corresponding value of an efficiency parameter relating to the blood depuration efficiency of the blood treatment unit. Notice that in order to perform the above calculation, the apparatus of FIG. 2 would need to create a perturbation either in the concentration of at least a substance or in the conductivity of the liquid upstream the treatment unit; to do so one solution could of course be to have 2 bags with different conductivities/concentration of at least a substance, both feeding line 14, and switch between them. Alternatively one could simply adopt a syringe for infusing a bolus of a known substance or mixture of substances in line 14.

As for FIG. 1, the efficiency parameter can be in-vivo clearance or change in the conductivity of the waste liquid.

The control unit is then programmed to control the flow rate of at least one or both of the fluid flows through said infusion lines as a function of said value of the efficiency parameter in a manner analogous to the one disclosed for FIG. 1, remembering that in case of FIG. 2 the control units acts directly on the pumps 26 and 27 to change flow rates in the respective infusion lines.

Though not representing today the most practical solution one could use change in the temperature in the waste liquid as a parameter describing treatment unit efficiency: in this case it would be necessary to create a temperature perturbation (or at least having a treatment liquid of temperature different from blood) in the liquid line 14 upstream the treatment unit (for instance by using a warmer or a bolus of solution injected in the liquid upstream the treatment unit), and of course providing for a temperature sensor for detecting temperature or temperature changes in the waste fluid flowing through waste line 12.

Alternatively to or even in combination with a TMP based control, the equipment of FIG. 2 could adopt a scale-based fluid control. In detail, the non-limiting embodiment shows use of a respective independent scale 29a, 30a, 31a, 32a for each corresponding separate container 29, 30, 31, 32. Each scale is connected to the control unit, via control lines 106, 107, 108, 109, and can serve to control one or more of the pumps 17, 18, 26, 27, and 28. The embodiment of FIG. 2 provides that each pump is controlled using the actual weights coming from the respective scale and a respective set value to achieve. Alternatively, the weight signals coming from more than one scale could be used to control one pump (typically the waste pump) in order to achieve the desired weight balance with no need of controlling all pumps. Also notice that alternatively to separate and independent scales 2 or more containers could be grouped on a single scale. In case all containers are on a single scale only knowledge and control of the overall fluid balance would be possible.

Notice that by using the scales both actual flow rate and absolute instant dispensed/collected fluid through each line are known; in other words the scales could be used as sensors of the fluid parameters (in this case flow rates through the respective lines), so the efficiency parameter could be determined also with formula (1). In other words the scales in this alternative would provide the control unite with weight information at regular intervals of time in order to allow the control unit to calculate the flow rates necessary for applying the above formula (1).

In scale-based control the machine could be programmed to freely modify pre and post infusion flow rates, while remaining within prefixed acceptable threshold ranges of TMP and of total infusion fluid, in order to maximize filter depuration efficiency. Also in this case, the equipment would start increasing for instance the pre-dilution and/or the post-dilution flow rate, then calculating a corresponding value of the efficiency parameter. In this case, after the flow modification, which results in an increased efficiency, the control unit would command a further change, which could occur either continuously or intermittently at time intervals during treatment.

Finally it is to be noted that control unit 21 can be implemented either by an analog control device or by a digital control device as a microprocessor with related memories. In this latter case the invention also comprises a software product including instructions designed for being executable by the control unit 21 and capable—when executed—of programming the control unit to perform the steps disclosed in detail in the description of embodiments 1 and 2. The instructions are stored on a data carrier such as a computer readable memory (by way of non limiting example a memory chip of the RAM, ROM, PROM or EPROM type can be used or a magnetic disk or an optical disk or any other convenient physical support can be equivalently used), an electric carrier signal, an electromagnetic carrier signal.

Variants to the above-disclosed embodiments could be devised without departing from the scope of the invention.

For instance alternative means can be devised for causing fluid flow through the lines. In detail, as far as blood flow is concerned, two blood pumps can be provided or a single blood pump operating either upstream or downstream the treatment unit, or in some cases the patient pressure can be used to move blood through the extra-corporeal circuit with no need of pumps.

With respect to the waste line one or more waste pumps are normally provided though in principle static pressure could be relied on with no need of any pumps but simply controlling fluid flow using controlled valves acting on the line.

In a similar manner, depending upon the situation, the dialysis liquid line could be provided with a pump associated therewith or with a regulating valve.

As to the infusion lines, the means for causing fluid flow could present several embodiments without departing from the scope of the invention. In detail, as mentioned, one or more infusion pumps could be operating on each respective infusion line. Alternatively, particularly when the infusion liquid source is common for the two infusion lines, either a respective pump on each respective line can be used or one pump combined with one or two flow regulators (such as valves or controlled tube restrictors) could be equivalently adopted. In greater detail, a single pump can be installed on a common portion of an infusion circuit, which then separate in two or more independent infusion lines provided with a respective flow regulator. The infusion fluid or fluids and/or the dialysis fluid can come from a solution container or be prepared online by the equipment 1. As to the waste line, it can be connected to a waste container or to a drain, depending upon the embodiment.

It is also to be noted that while the embodiments herein disclosed shown use of only one pre-infusion line and of only one post-infusion line, the invention could be applied even if more pre or post infusion lines would be adopted.

With reference to the efficiency parameter, it can be calculated from values of one among various physical or chemical parameters of the waste fluid. Depending upon the embodiments, the waste fluid parameter can be one of the following: conductivity of the waste fluid, or concentration of at least one substance contained in the waste fluid, or flow rate of the waste fluid, or temperature of the waste fluid, or density of the waste fluid, or viscosity of the waste fluid or even a parameter known function of one of the above listed parameters.

As described if the efficiency parameter is in-vivo clearance, then any method for in-vivo determination of clearance can be used and at this purpose a conductivity or a concentration sensor is used on the waste line do detect either concentration of at east a substance or conductivity of the waste liquid to then calculate clearance therefrom.

However also formula (1) in case flows are known: notice flows can be detected with flow sensors (for instance using a flow sensor on each line the flow through which is to be determined), or can be calculated by the control unit knowing the and as a function of rotation speed of each pump, or can be determined by the control unit starting from the weight detections of scales (see for instance embodiment of FIG. 2), or could be obtained combining one or more of the techniques just listed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Reference Number List equipment 1
extracorporeal blood circuit 2
arterial line 3
venous line 4
first chamber inlet 5
first chamber 6
treatment unit 7
second chamber 8
semipermeable membrane 9
first chamber outlet 10
second chamber outlet 11
waste line 12
second chamber inlet 13
dialysis liquid line 14
pre-infusion line 15
post-infusion line 16
blood pump 17
waste pump 18
fresh liquid pump 19
distribution device 20
control unit 21
venous pressure sensor 22
dialysate pressure sensor 23
flow meters 24 and 25
pumps 26, 27, 28
waste container 29
first infusion container 30
second infusion container 31
dialysis fluid container 32
waste fluid parameter sensor 33 sensor 34
common portion 35
control lines 101, 102, 102, 103, 104 and 105.
control lines 106, 107, 108, 109

What is claimed is:

1. A method for controlling infusion in a blood treatment equipment, said equipment comprising:
   an extracorporeal blood circuit having at least one blood treatment unit presenting a first and a second chamber separated by a semipermeable membrane, a pre-infusion line connected to the blood circuit upstream of the blood treatment unit, a post-infusion line connected to the blood circuit downstream of the blood treatment unit, and
   a waste line connected to an outlet of the second chamber for receiving waste fluid exiting out of the second chamber; said method comprising the steps of:
   causing a fluid flow through said pre-infusion line,
   causing a fluid flow through said post-infusion line,
   determining values of at least one parameter of the waste fluid in said waste line, calculating from said values of the at least one waste fluid parameter at least a corresponding value of an efficiency parameter relating to blood depuration efficiency of the blood treatment unit, and
   controlling the flow rate of at least one of the fluid flows through said pre-infusion and post-infusion lines as a function of said value of the efficiency parameter, wherein said controlling step comprises the following timely consecutive sub-steps:
   determining a pre-change value of the efficiency parameter,
   increasing the flow rate through at least one of the infusion lines,
   determining a post-change value of the efficiency parameter,
   comparing the pre-change and the post-change values of the efficiency parameter and if, as a result of said comparison, the post-change value of the efficiency parameter is higher than the pre-change value of the efficiency parameter, then increasing again the flow rate of said at least one of the infusion lines,
   the sub-steps of increasing the flow rate, determining a post-change value and comparing the pre and post change values being repeated until no further gain in the efficiency parameter can be achieved.

2. A method according to claim 1, wherein said waste fluid parameter is one selected in the group comprising:
   conductivity of the waste fluid, concentration of at least one substance contained in the waste fluid, flow rate of the waste fluid, temperature of the waste fluid, density of the waste fluid, viscosity of the waste fluid, a parameter known function of the conductivity of the waste fluid,
   a parameter known function of the concentration of at least one substance contained in the waste fluid, a parameter known function of the flow rate of the waste fluid,
   a parameter known function of the temperature of the waste fluid a parameter known function of density of the waste fluid, or a parameter known function of viscosity of the waste fluid.

3. A method according to claim 1, wherein the controlling step comprises controlling both the flow rate through the pre-infusion line and the flow rate through the post-infusion line as a function of said value of the efficiency parameter.

4. A method according to claim 1, wherein said timely consecutive steps are continuously repeated at regular time intervals during treatment.

5. A method according to claim 1, wherein said controlling step, in correspondence with said increasing the flow rate through at least one of the infusion lines comprises contemporaneously decreasing the flow rate of the other infusion line.

6. A method according to claim 1, wherein said controlling step comprises controlling that the maximum total infusion rate through said pre and post infusion lines does not exceed a prefixed threshold.

7. A method according to claim 1, wherein said controlling step comprises keeping substantially constant the maximum total infusion rate through said pre and post infusion.

8. A method according to claim 1, wherein said controlling step provides for keeping a trans membrane pressure across said semi-permeable membrane substantially following a pre-set profile.

9. A method according to claim 1, wherein the determination of the value of the efficiency parameter comprises the steps of receiving signals relating to values of said waste fluid parameter and calculating from said signals at least a corresponding value of the efficiency parameter relating to the blood depuration efficiency of the blood treatment unit.

10. A method according to claim 9, wherein the efficiency parameter is one selected in the group comprising: an electrolyte dialysance, a metabolite clearance, a parameter which is function of an electrolyte dialysance, a parameter which is function of a metabolite clearance.

11. Blood treatment equipment, comprising:
    an extracorporeal blood circuit having at least one blood treatment unit presenting a first and a second chamber separated by a semipermeable membrane,
    a pre-infusion line connected to the blood circuit upstream the blood treatment unit,
    a post-infusion line connected to the blood circuit downstream the blood treatment unit,
    a waste line connected to an outlet of the second chamber for receiving fluid exiting out of the second chamber,
    means for determining values of at least a parameter of the waste fluid, means for causing a flow rate through said infusion lines,
    a control unit connected to the means for determining a parameter of the waste fluid and connected to the means for creating a flow rate, said control unit being programmed to execute the following control unit steps:
    receiving signals relating to values of said waste fluid parameter
    acting on said means for causing a fluid flow through said pre-infusion line and through said post-infusion line,
    calculating from said values of the waste fluid parameter at least a corresponding value of an efficiency parameter relating to the blood depuration efficiency of the blood treatment unit, and
    controlling the flow rate of at least one of the fluid flows through said infusion lines as a function of said value of the efficiency parameter, wherein said controlling step comprises the following timely consecutive steps:
    determining a pre-change value of the efficiency parameter,
    modifying the flow rate of the fluid through at least one of the infusion lines,
    determining a post-change value of the efficiency parameter after the modifying step, and
    comparing the pre-change and the post-change values of the efficiency parameter and if, as a result of said comparison, the post-change value of the efficiency parameter is higher than the pre-change value of the efficiency parameter, then increasing again the flow rate of said at least one of the infusion lines,
the sub-steps of increasing the flow rate, determining a post-change value and comparing the pre and post change values being repeated until no further gain in the efficiency parameter can be achieved.

12. Blood treatment equipment according to claim 11, wherein said waste fluid parameter is one selected in the group comprising:
conductivity of the waste fluid, concentration of at least one substance contained in the waste fluid, flow rate of the waste fluid, temperature of the waste fluid, density of the waste fluid, viscosity of the waste fluid, a parameter known function of the conductivity of the waste fluid, a parameter known function of the concentration of at least one substance contained in the waste fluid, a parameter known function of the flow rate of the waste fluid, a parameter known function of the temperature of the waste fluid a parameter known function of density of the waste fluid, or a parameter known function of viscosity of the waste fluid.

13. Blood treatment equipment according to claim 11, wherein during said controlling step the control unit controls both the flow rate through the pre-infusion line and the flow rate through the post-infusion line as a function of said value of the efficiency parameter.

14. Blood treatment equipment according to claim 11, wherein said timely consecutive steps are continuously repeated at regular time intervals during treatment.

15. Blood treatment equipment according to claim 14, wherein said controlling step, in correspondence of said increasing the flow rate through at least one of the infusion lines comprises contemporaneously decreasing the flow rate of the other of infusion line.

16. Blood treatment equipment according to claim 11, wherein said controlling step comprises controlling that the maximum total infusion rate through said pre and post infusion lines does not exceed a prefixed threshold.

17. Blood treatment equipment according to claim 11, wherein said controlling step comprises keeping substantially constant the maximum total infusion rate through said pre and post infusion.

18. Blood treatment equipment according to claim 11, wherein said controlling step provides for keeping a trans membrane pressure across said semi-permeable membrane substantially following a pre-set profile.

19. Blood treatment equipment according to claim 11, wherein the efficiency parameter is one selected in the group comprising: an electrolyte dialysance, a metabolite clearance, a parameter function of an electrolyte dialysance, a parameter function of a metabolite clearance.

20. A method for controlling infusion in a blood treatment equipment, said equipment comprising:
an extracorporeal blood circuit having at least one blood treatment unit presenting a first and a second chamber separated by a semipermeable membrane,
a pre-infusion line connected to the blood circuit upstream of the blood treatment unit,
a post-infusion line connected to the blood circuit downstream of the blood treatment unit, and
a waste line connected to an outlet of the second chamber for receiving waste fluid exiting out of the second chamber; said method comprising the steps of:
causing a fluid flow through said pre-infusion line,
causing a fluid flow through said post-infusion line,
determining values of at least one parameter of the waste fluid in said waste line, said waste fluid parameter being one selected in the group comprising:
conductivity of the waste fluid,
concentration of at least one substance contained in the waste fluid,
flow rate of the waste fluid,
temperature of the waste fluid,
density of the waste fluid,
viscosity of the waste fluid,
a parameter being a function of the conductivity of the waste fluid,
a parameter being a function of the concentration of at least one substance contained in the waste fluid,
a parameter being a function of the flow rate of the waste fluid,
a parameter being a function of the temperature of the waste fluid a parameter known function of density of the waste fluid, or
a parameter being a function of viscosity of the waste fluid;
determining from said values of the at least one waste fluid parameter at least a corresponding value of an efficiency parameter relating to blood depuration efficiency of the blood treatment unit, the determination of the value of the efficiency parameter including receiving signals relating to values of said waste fluid parameter and calculating from said signals at least a corresponding value of the efficiency parameter relating to the blood depuration efficiency of the blood treatment unit, the efficiency parameter being one selected in the group comprising: an electrolyte dialysance, and a metabolite clearance;
comparing said calculated corresponding value of the efficiency parameter with a determined value of the efficiency parameter; and
controlling both the flow rate through the pre-infusion line and the flow rate through the post-infusion line as a function of said comparison.

21. A method according to claim 20, wherein said controlling of the flow rate through the pre-infusion line and the post-infusion line is carried out as a function of a change over time of the value of said efficiency parameter.

22. A method according to claim 20, wherein said controlling step comprises the following timely consecutive steps:
determining a pre-change value of the efficiency parameter,
modifying the flow rate of the fluid through at least one of the infusion lines,
determining a post-change value of the efficiency parameter after the modifying step, and
comparing the pre-change and the post-change values of the efficiency parameter.

23. A method according to claim 22, wherein said timely consecutive steps are continuously repeated at regular time intervals during treatment.

24. A method according to claim 22, wherein said step of modifying the flow rate comprises increasing the flow rate of at least one of the infusion lines.

25. A method according to claim 24, wherein said step of modifying the flow rate comprises contemporaneously decreasing the flow rate of the other infusion line.

26. A method according to claim 25, wherein if as a result of said comparison the post-change value of the efficiency parameter is higher than the pre-change value of the efficiency parameter, then the flow rate through said at least one of the infusion lines is increased again, contemporaneously decreasing the flow rate through the other infusion line.

27. A method according to claim 24, wherein if as a result of said comparison the post-change value of the efficiency parameter is higher than the pre-change value of the efficiency parameter, then the flow rate of said at least one of the infusion lines is increased again.

28. A method according to claim 22, wherein said controlling step comprises controlling that the maximum total infusion rate through said pre and post infusion lines does not exceed a prefixed threshold.

29. A method according to claim 22, wherein said controlling step comprises keeping substantially constant the maximum total infusion rate through said pre and post infusion.

30. A method according to claim 22, wherein said controlling step provides for keeping a trans membrane pressure across said semi-permeable membrane substantially following a pre-set profile.

31. A method according to claim 20, wherein said controlling step comprises the following timely consecutive steps:
modifying the flow rate of the fluid through at least one of the infusion lines, determining a post-change value of the efficiency parameter after the modifying step, and
comparing the post-change value of the efficiency parameter with a set value.

32. A method according to claim 31, wherein said timely consecutive steps are continuously repeated at regular time intervals during treatment.

33. A method according to claim 31, wherein said step of modifying the flow rate comprises increasing the flow rate of at least one of the infusion lines.

34. A method according to claim 33, wherein said step of modifying the flow rate comprises contemporaneously decreasing the flow rate of the other infusion line.

35. A method according to claim 34, wherein if as a result of said comparison the post-change value of the efficiency parameter is higher than the set value of the efficiency parameter, then the flow rate through said at least one of the infusion lines is increased, contemporaneously decreasing the flow rate through said other infusion line.

36. A method according to claim 33, wherein if as a result of said comparison the post-change value of the efficiency parameter is higher than the set value of the efficiency parameter, then the flow rate of said at least one of the infusion lines is increased again.

37. A method according to claim 31, wherein said controlling step comprises controlling that the maximum total infusion rate through said pre and post infusion lines does not exceed a prefixed threshold.

38. A method according to claim 31, wherein said controlling step further comprises keeping substantially constant the maximum total infusion rate through said pre and post infusion.

39. A method according to claims 31, wherein said controlling step further provides for keeping a trans-membrane pressure across said semi-permeable membrane substantially following a pre-set profile.

40. Blood treatment equipment, comprising:
an extracorporeal blood circuit having at least one blood treatment unit presenting a first and a second chamber separated by a semipermeable membrane,
a pre-infusion line connected to the blood circuit upstream the blood treatment unit,
a post-infusion line connected to the blood circuit downstream the blood treatment unit,
a waste line connected to an outlet of the second chamber for receiving fluid exiting out of the second chamber,
means for determining values of at least a parameter of the waste fluid, said waste fluid parameter being one selected in the group comprising:
conductivity of the waste fluid,
concentration of at least one substance contained in the waste fluid,
flow rate of the waste fluid,
temperature of the waste fluid,
density of the waste fluid,
viscosity of the waste fluid,
a parameter being a function of the conductivity of the waste fluid,
a parameter being a function of the concentration of at least one substance contained in the waste fluid,
a parameter being a function of the flow rate of the waste fluid,
a parameter being a function of the temperature of the waste fluid a parameter known function of density of the waste fluid, or
a parameter being a function of viscosity of the waste fluid;
means for causing a flow rate through said infusion lines,
a control unit connected to the means for determining a parameter of the waste fluid and connected to the means for creating a flow rate, said control unit being programmed to execute the following control unit steps:
receiving signals relating to values of said waste fluid parameter
acting on said means for causing a fluid flow through said pre-infusion line and through said post-infusion line,
calculating from said values of the waste fluid parameter at least a corresponding value of an efficiency parameter relating to the blood depuration efficiency of the blood treatment unit, the efficiency parameter being one selected in the group comprising: an electrolyte dialysance, and a metabolite clearance,
comparing said calculated corresponding value of the efficiency parameter with a determined value of the efficiency parameter; and
controlling both the flow rate through the pre-infusion line and the flow rate through the post-infusion line as a function of said comparison.

41. Blood treatment equipment according to claim 40, wherein said controlling of the flow rate through at least one of the pre-infusion line and the post-infusion line is carried out as a function of the change over time of the value of said efficiency parameter.

42. Blood treatment equipment according to claim 40, wherein said controlling step comprises the following timely consecutive steps:
determining a pre-change value of the efficiency parameter,
modifying the flow rate of the fluid through at least one of the infusion lines,
determining a post-change value of the efficiency parameter after the modifying step, and
comparing the pre-change and the post-change values of the efficiency parameter.

43. Blood treatment equipment according to claim 42, wherein said timely consecutive steps are continuously repeated at regular time intervals during treatment.

44. Blood treatment equipment according to claim 42, wherein said step of modifying the flow rate comprises increasing the flow rate of at least one of the infusion lines.

45. Blood treatment equipment according to claim 44, wherein said step of modifying the flow rate comprises contemporaneously decreasing the flow rate of the other of infusion line.

46. Blood treatment equipment according to claim 42, wherein if as a result of said comparison the post-change value of the efficiency parameter is higher than the pre-change value of the efficiency parameter, then increasing again the flow rate of said at least one of the infusion lines.

47. Blood treatment equipment according to claim 42, wherein said controlling step comprises controlling that the maximum total infusion rate through said pre and post infusion lines does not exceed a pre-fixed threshold.

48. Blood treatment equipment according to claim 42, wherein said controlling step comprises keeping substantially constant the maximum total infusion rate through said pre and post infusion.

49. Blood treatment equipment according to claim 42, wherein said controlling step provides for keeping a transmembrane pressure across said semi-permeable membrane substantially following a pre-set profile.

50. Blood treatment equipment according to claim 40, wherein said controlling step comprises the following timely consecutive steps:
modifying the flow rate of the fluid through at least one of the infusion lines,
determining a post-change value of the efficiency parameter after the modifying step, and
comparing the post-change value of the efficiency parameter with a set value.

51. Blood treatment equipment according to claim 50, wherein said timely consecutive steps are continuously repeated at regular time intervals during treatment.

52. Blood treatment equipment according to claim 50, wherein said step of modifying the flow rate comprises increasing the flow rate of at least one of the infusion lines.

53. Blood treatment equipment according to claim 52, wherein said step of modifying the flow rate comprises contemporaneously decreasing the flow rate of the other of infusion line.

54. Blood treatment equipment according to claim 50, wherein if as a result of said comparison the post-change value of the efficiency parameter is higher than the set value of the efficiency parameter, then increasing again the flow rate of said at least one of the infusion lines.

55. Blood treatment equipment according to claim 50, wherein said controlling step comprises controlling that the maximum total infusion rate through said pre and post infusion lines does not exceed a prefixed threshold.

56. Blood treatment equipment according to claim 50, wherein said controlling step comprises keeping substantially constant the maximum total infusion rate through said pre and post infusion.

57. Blood treatment equipment according to claim 50, wherein said controlling step provides for keeping a transmembrane pressure across said semi-permeable membrane substantially following a pre-set profile.

* * * * *